United States Patent
Zhang et al.

(10) Patent No.: US 8,951,568 B2
(45) Date of Patent: Feb. 10, 2015

(54) GRANULE AND PREPARATION METHOD THEREOF

(75) Inventors: Shunnan Zhang, Tianjin (CN); Jianhui Yang, Tianjin (CN); Lina Dong, Tianjin (CN); Hongbo Zhang, Tianjin (CN); Xiaolin Bai, Tianjin (CN); Yan Sun, Tianjin (CN); Ting Li, Tianjin (CN)

(73) Assignee: Tasly Pharmaceuticals Group Co., Ltd., Zhongyao, Tianjin (CN)

( * ) Notice: Subject to any disclaimer, the term of this patent is extended or adjusted under 35 U.S.C. 154(b) by 428 days.

(21) Appl. No.: 12/306,371

(22) PCT Filed: Jun. 22, 2007

(86) PCT No.: PCT/CN2007/001960
§ 371 (c)(1),
(2), (4) Date: Aug. 4, 2009

(87) PCT Pub. No.: WO2008/000166
PCT Pub. Date: Jan. 3, 2008

(65) Prior Publication Data
US 2010/0009000 A1    Jan. 14, 2010

(30) Foreign Application Priority Data
Jun. 23, 2006  (CN) .......................... 2006 1 0014409

(51) Int. Cl.
| A61K 9/14 | (2006.01) |
| A01N 65/00 | (2009.01) |
| A61K 36/00 | (2006.01) |
| A61K 9/50 | (2006.01) |
| A61K 9/16 | (2006.01) |
| A61K 36/233 | (2006.01) |

(52) U.S. Cl.
CPC ............. *A61K 9/5078* (2013.01); *A61K 9/5089* (2013.01); *A61K 9/1676* (2013.01); *A61K 9/1682* (2013.01); *A61K 36/233* (2013.01)
USPC .......................... 424/497; 424/494; 424/725

(58) Field of Classification Search
None
See application file for complete search history.

(56) References Cited

U.S. PATENT DOCUMENTS

| 4,350,688 A * | 9/1982 | Schmittmann .................. 514/26 |
| 2004/0081691 A1* | 4/2004 | Debregeas et al. ........... 424/465 |
| 2006/0093680 A1* | 5/2006 | Humar et al. .................. 424/490 |
| 2006/0153917 A1 | 7/2006 | Ullah et al. |
| 2008/0193544 A1* | 8/2008 | Bruck-Scheffler et al. ... 424/493 |
| 2012/0034304 A1* | 2/2012 | Bartholomaeus et al. .... 424/484 |

FOREIGN PATENT DOCUMENTS

| CN | 1109779 A | 10/1995 |
| CN | 1736406 A | 2/2006 |
| EP | 1088789 A2 | 4/2001 |
| JP | 55-092313 A | 7/1980 |
| JP | 2-167229 A | 6/1990 |
| JP | 2-174722 A | 7/1990 |
| JP | 6-192113 A | 7/1994 |
| JP | 7-309769 A | 11/1995 |
| JP | 2002-544220 A | 12/2002 |
| RU | 2349319 C1 | 3/2009 |
| WO | 0069414 A2 | 11/2000 |

OTHER PUBLICATIONS

Search Report issued in European Patent Application No. 07 721 533.3, dated Jan. 28, 2010, 8 pages.
Gao, C., et al., "Method for Preparing Formulation Containing Extract of Indian Mulberry," Chemical Abstracts Online, Database Accession No. 2006:240728, Abstract for CN 1736406, Chemical Abstracts Service, Columbus, Ohio, US, 1 page.
Yu, L., et al., "A Chinese Medicinal Granule for Treating Hepatitis, and Method for Preparing the Same," Chemical Abstracts Online, Database Accession No. 2005:885908, Abstract for CN 1109779, Chemical Abstracts Service, Columbus, Ohio, US, 1 page.
Chueshov, V.I., et al., "Industrial Technology of Medicines Book 2, Chapter 14.6. Granulation in Conditions of Fluidization," 2002, MTK-Book, NFAU Publishing House, 3 pages (6 pages with translation).
Krasniuk, I.I., et al., "Pharmaceutical Technology. Technology of Medicines," 2006, 2nd Ed., Academy Publishing Center, p. 545.

* cited by examiner

*Primary Examiner* — H. Sarah Park
(74) *Attorney, Agent, or Firm* — Senniger Powers LLP

(57) ABSTRACT

A pharmaceutical granule whose shape is spherical or sphere-like shape with a bulk density of 0.6-1.3 g/ml and a dissolution time of 0.5-5 minutes, which is prepared as follows: mother granules are filled into a fluidized-bed as bed charge; active pharmaceutical ingredients are prepared into a suspension or solution whose viscosity is adjusted to 6.0-9.8 Mpa·S with viscosity adjusting agent; then it is sprayed onto surface of said mother granule to obtain final granule.

3 Claims, No Drawings

GRANULE AND PREPARATION METHOD THEREOF

FIELD OF THE INVENTION

The present invention relates to a pharmaceutical preparation and a preparation method thereof, wherein said pharmaceutical preparation refers to granules, especially granules of Traditional Chinese Medicine (TCM) or herbal medicine and a preparation method thereof.

BACKGROUND OF THE INVENTION

Traditionally, granule of TCM or herbal medicine is prepared from TCM, herbal medicine or their extract by dry granulating method or wet granulating method to produce granular material with certain particle diameter. When administered, it is taken after being mixed with water or swallowed. Due to the high viscosity of the extractum of TCM or herbal medicine, such shortcomings exist in most granules prepared by conventional granulating method as low drug loading, unsatisfactory appearance, poor taste and high moisture absorption, etc. By the current popular fluidized-bed granulating technique, various carriers are placed in the container alone or in combination with pharmaceutical powder, and air at proper temperature is insufflated through the sieve plate from the bottom of bed to well mix the material in fluid condition, then solution of binder is evenly sprayed into. Accordingly, the powder begins to agglomerate to obtain granule. After repeated spraying and drying, granules with desired particle diameter are produced, then stopping spraying, and continuing to dry. This process can decrease the amount of carrier from the conventional 80 wt % to less than 50 wt % and also decrease single dose of the granule from 10 g to 3-5 g. However, this process can neither solve problems caused by high viscosity of extract of TCM or herbal medicine, nor further decrease the amount of carrier. Therefore, these disadvantages such as high single dose and poor compliance of patients exist in the granule prepared by the process. Also, these granules are unsuitable to be prepared into solid preparation such as capsules etc. In addition, the granules prepared by this method are porous and irregular in shape, and commonly has shortcoming of moisture absorption, accordingly it is inconvenient to store these granules. Due to the high specific surface area, such granules are unsuitable to be coated.

Currently, there are also researches to produce micro-pills with a particle diameter of 700-1500 μm using extract of TCM or herbal medicine by fluidized-bed granulation process. However, according to this process, medicines are made into dry powder, which is added while spraying water or other liquid mixture as binder to produce micro-pills. The micro-pills prepared by this process commonly have a dissolution time of 40 minutes. In addition, the process is complex, high-cost and high-consuming with many affecting factors (for example, it can not be performed in the condition of high air-humidity).

Additionally, extrusion-rounding method or extrusion-spheronization method is also used to produce micro-pills or spherical granules in the pharmaceutical field. Products by this method consume a large amount of carrier with a drug loading of less than 25% and a dissolution time of more than 30 minutes.

In the art of dosage form, fluidized-bed granulation processes by bottom spraying or side spraying have been used to produce micro-pills or spherical granules of chemical medicine. Most of them are used to develop sustaining-release preparations. So, the products prepared by the processes are usually sustaining-released or controlled-released instead of rapid released.

The rapid release and rapid onset of therapeutic effect of TCM are important aspects of TCM modernization. The granules of TCM or herbal medicine provided in the present invention have the property of rapid dissolution.

SUMMARY OF THE INVENTION

One objective of the present invention is to provide a pharmaceutical granule, especially a granule of TCM or herbal medicine, said granule has such advantages as low single dose, short dissolution time, convenient to be stored and satisfactory appearance. Said granule can also be used as intermediate to prepare capsules and tablets.

The granule of the present invention includes mother granule and shell layer outside the mother granule with active pharmaceutical ingredients contained in the mother granule and/or the shell layer, whose shape is spherical or sphere-like with a bulk density of 0.6-1.3 g/ml and a dissolution time of 0.5-5 minutes. Preferably, the active pharmaceutical ingredients are contained in the shell layer or both the mother granule and the shell layer. Said active pharmaceutical ingredients can be any chemical medicine, TCM, herbal medicine or their extract, preferably, the active pharmaceutical ingredients are TCM, herbal medicine or their extract. According to the setting of dosage form in Chinese Pharmacopoeia (Edition 2005), also in order to distinguish the granule of the present invention from micro-pill and micro-capsule etc., and said granule is called as "spherical granule" when taking into account of the properties of the product prepared by the process.

In the above mentioned spherical granule, said mother granule comprises pharmaceutically acceptable carrier and/or the extract of TCM or herbal medicine, and the mother granule has a particle diameter of 200-750 μm.

Said shell layer comprises extract of TCM or herbal medicine and pharmaceutically acceptable carrier.

The pharmaceutically acceptable carrier in the mother granule and the shell layer can be any common or conventional pharmaceutically acceptable carrier used in the preparation of granule of TCM or herbal medicine, for example, diluents (fillers), including but not limited to sucrose, dextrin, starch, lactose, mannitol, xylitol, chitosan, bidismutose (a saccharide having a health-care function to reproduce *Bacillus bifidus*), soluble starch, talc powder or water-soluble dextrin, etc.; disintegrating agents, including but not limited to starch, sodium carboxy methyl starch (CMS-Na), microcrystalline cellulose (MCC), micro-powder silica gel, hydroxypropyl starch, soluble starch or water-soluble dextrin; inclusion agents, including but not limited to α-cyclodextrin (α-CD), β-cyclodextrin (β-CD) and N-LOK modified starch; wetting agents (binders), including but not limited to water, ethanol, polyvinylpyrrolidone (polyvidon, PVP), hydroxypropyl methyl cellulose, polyethylene glycol (PEG), microcrystalline cellulose, micro-powder silica gel, talc powder and chitosan, etc. The wetting agents, according to their function, herein are called as "viscosity adjusting agent", can be any common or conventional pharmaceutically acceptable carrier used in preparing granule of TCM medicine or herbal medicine. Preferable, the viscosity adjusting agent is selected from the group consisting of microcrystalline cellulose, micro-powder silica gel, polyethylene glycol, talc powder, chitosan, polyvidon, and hydroxypropyl methyl cellulose. The above mentioned pharmaceutically acceptable carrier can be used alone or in combination. It can be understood by the skilled in the art that the pharmaceutically acceptable carrier which will emerge in the future is also included in the scope of the present invention as long as it can achieve the objective of the present invention. Relative to the total weight of the spherical granule, the content of the pharmaceutically acceptable carrier can be adjusted according to the properties of the product. It may be 10-60 wt %, preferably 20-30 wt %. The dissolution time of such prepared spherical granule is short, usually about 0.5-5 minutes.

The extract of TCM or herbal medicine contained in the mother granule and the shell layer may be extractum or composition of effective fractions, and it also may be monomer. Said extracts can be prepared by any common or conventional methods in the art, for example, decocting method, dipping method, percolating method, refluxing method, water extracting and ethanol precipitation method and ethanol extracting and water precipitation method, etc. Also said extracts can be prepared by the methods in prior art. Said extracts can be treated by purification process if needed, wherein purification process can be any common or conventional methods such as ultra-filtration or macro-porous resin method, etc. Also, said extracts can be purified by the purification process in prior art. Of course, the extract of TCM or herbal medicine can also be purchased commercially as long as the quality can satisfy the need of the present invention. It can be understood by the skilled in the art that extract of TCM or herbal medicine can also be prepared by new techniques which will emerge in the future.

According to the present invention, the particle diameter of the spherical granule preferably is 700-1500 μm.

According to the present invention, the spherical granule can also comprise coating layer and the amount of the coating agents accounts for 2-5 wt % of the total weight of the coated granule. When the spherical granule is coated, the amount of the coating agent used is markedly lower than that of conventional granule, i.e. the amount of the coating agents in conventional granule accounts for 20-30 wt % of the total weight of the coated granule, while the amount of the coating agents in the spherical granule of the present invention can decreased to 2-5 wt %. Based on actual needs, the coating may be common film coating, and also be enteric film coating or sustaining-release or control-release coating, etc. The coating agents may be any common or conventional coating agents in the art which are selected depending on different needs. The coating process may be carried out according to conventional methods in the art.

The spherical granule according to the present invention can be directly used as common granules, and it can be used as intermediate to prepare such dosage form as capsule, or used as formula granule. In addition, it can also be prepared into sustaining-release or control-release preparations or site-specific sustaining-release preparations, etc.

Another objective of the present invention is to provide a preparation process of the above mentioned granule.

The spherical granule according to the present invention is prepared by fluidized-bed technique by selecting proper pharmaceutically acceptable carrier as viscosity adjusting agent; the viscosity adjusting agent is selected based on properties of the extract of TCM or herbal medicine such as viscosity, film forming ability, strength and severity of producing powder etc. A preparation method of the granule of the present invention comprises the following steps:
 (1) Filling mother granules into a container of a fluidized-bed as bed charge;
 (2) Insufflating gas-flow;
 (3) Preparing active pharmaceutical ingredients into a viscous suspension or solution, spraying the suspension or solution as slurry onto surface of said mother granule to form shell layer and obtain the granule.

The preparation process of the spherical granule according to the present invention is performed according to conventional fluidized-bed granulation process in the art.

Said pharmaceutically acceptable carrier used in the preparation process of the spherical granule can be any common or conventional pharmaceutically acceptable carrier used in the preparation of granule of TCM or herbal medicine, for example, diluents (fillers), including but not limited to sucrose, dextrin, starch, lactose, mannitol, xylitol, chitosan, bidismutose (a saccharide having a health-care function to reproduce *Bacillus bifidus*), soluble starch, talc powder or water-soluble dextrin, etc.; disintegrating agents, including but not limited to starch, sodium carboxy methyl starch (CMS-Na), microcrystalline cellulose (MCC), micro-powder silica gel, hydroxypropyl starch, soluble starch or water-soluble dextrin; inclusion agents, including but not limited to α-cyclodextrin (α-CD), β-cyclodextrin (β-CD) and N-LOK modified starch; wetting agents (binders), including but not limited to water, ethanol, polyvinylpyrrolidone (polyvidon, PVP), hydroxypropyl cellulose, polyethylene glycol (PEG), microcrystalline cellulose, micro-powder silica gel, talc powder and chitosan. The wetting agents, according to their function, herein are called as "viscosity adjusting agent" preferably is microcrystalline cellulose, micro-powder silica gel, polyethylene glycol, talc powder, chitosan and polyvidon. The above mentioned pharmaceutically acceptable carrier can be used alone or in combination. It can be understood by the skilled in the art that the pharmaceutically acceptable carrier which will emerge in the future is also included in the scope of the present invention as long as it can achieve the objective of the present invention. Generally, the particle diameter of the granule is required to be able to pass through 200 mesh sieve. The temperature during the preparation process may vary depending on the materials, and it may be 40-75° C., preferably 40-55° C., more preferably 45° C.

Usually, powder material is directly filled into a container of a fluidized-bed as bed charge in common fluidized-bed granulating process, but mother granule with a certain particle diameter is used as bed charge in the present invention, as described in step (1). Said mother granule can be prepared from pharmaceutically acceptable carrier alone, or be prepared from the mixture of pharmaceutically acceptable carrier and dry powder of extract of TCM or herbal medicine. Said mother granule can be prepared by the following steps:
 (i) Grinding the pharmaceutically acceptable carrier or the mixture of said pharmaceutically acceptable carrier and dry powder of the extract of TCM or herbal medicine, passing through a 200 mesh sieve to obtain a material satisfying the requirement for particle diameter;
 (ii) Filling a portion of said material obtained in step (i) into a side-spraying or bottom-spraying spot of a fluidized-bed, again taking the pharmaceutically acceptable carrier and/or and the extract of TCM or herbal medicine and adding water to prepare into slurry, then spraying the slurry into the fluidized-bed by side-spraying or bottom-spraying process, and screening out small particles as mother cores, thereafter putting the mother cores into the spot and continue to spray said slurry, simultaneously dusting the residual material obtained in step (i) in fine powder form using dusting gun to enable the mother cores to grow, then selecting the mother granule with desired particle diameter.

In step (i) of the preparation of the mother granule, the type and content of said pharmaceutically acceptable carrier can be any common or conventional pharmaceutically acceptable carrier used in preparing granule of TCM or herbal medicine.

In step (ii) of the preparation of the mother granule, the particle diameter of the mother core preferably is 180-250 μm and the particle diameter of the mother granule can be 200-750 μm. The proportion of the material in step (i) for preparing the mother cores can be adjusted depending on the viscosity of the material. The solid content in said slurry can be adjusted to 5-20 wt %. The particle diameter of the mother granule prepared can be selected depending on the requirement of the product. Generally, when the content of the extract of TCM or herbal medicine in final product is high, the mother granule with a particle diameter of 200-400 μm can be selected to avoid high intake level. Otherwise, the mother granule with a particle diameter of 400-750 μm can be selected.

The mother granule of the present invention can also be prepared by extrusion-spheronization method. Of course, the mother granule with desired particle diameter can also be purchased commercially.

In the preparation method according to the present invention, the suspension or solution used in step (3) should have a certain viscosity. A viscosity adjusting agent is added into a diluent of extract of TCM or herbal medicine to adjust its viscosity. The viscosity adjusting agent is selected based on properties of the extract of TCM or herbal medicine such as viscosity, film forming ability, strength and severity of producing powder, etc. The viscosity of said suspension or solution in step (3) is adjusted by the following steps:

(a) Diluting the extract of TCM or herbal medicine to obtain a diluent;
(b) Dropping 1-2 drops of the diluent on slide glass, airing, and evaluating such properties as viscosity, film forming ability, strength, severity of producing powder on surface of solid scar after evaporation of liquid;
(c) Adjusting the viscosity of the diluent of step (a) with a viscosity adjusting agent, and the viscosity adjusting agent is selected based on such properties as viscosity, film forming ability, strength and severity of producing powder of the scar;
(d) Repeating step (b) and step (c) until a solution or suspension with desired viscosity is obtained.

In step (a), the extract of TCM or herbal medicine is diluted by the diluting agent, and the diluting agent is selected from the group consisting of water, ethanol, ethanol aqueous solution or other organic solvent which is commonly used in pharmaceutical field as liquid diluting agent;

In step (c), the viscosity adjusting agent can be any common or conventional pharmaceutically acceptable carrier used in preparing granule of TCM or herbal medicine, preferably it is selected from the group consisting of microcrystalline cellulose, micro-powder silica gel, polyethylene glycol, talc powder, chitosan, polyvidon and hydroxypropyl methylcellulose, used alone or in combination.

In step (d), the solid content of the obtained solution or suspension is 10-60 wt %, preferably 15-40 wt %, and the viscosity is 6.0-9.8 Mpa·S.

The viscosity adjusting agent is evaluated and selected according to the method of step (b). More specifically, it is performed as follows: taking the adjusted solution or suspension of step (c), evaluating its viscosity according to the method of step (b), and determining the type and the viscosity of the viscosity adjusting agent. The type and content of the carrier should be determined according to the formulation of the desired granule product, and it is easy for the skilled in the art after simple tests.

The selected pharmaceutically acceptable carrier is added as viscosity adjusting agent to the diluent of the extract of TCM or herbal medicine to adjust the viscosity, the suspension or solution is obtained and sprayed as slurry on the surface of the mother granule to form said shell layer.

The value of viscosity in the present invention can be obtained according to conventional methods, for example it can be measured using NDJ-79 Viscometer (Shanghai Changji Geological Instrument Co., Ltd.). The value of dissolution time in the present invention can be obtained according to conventional methods, for example it can be measured by the method for determining dissolution time described in Item of Pills in Appendix IA, Vol. I, Chinese Pharmacopoeia. The value of particle diameter in the present invention can be obtained according to conventional methods, for example it can be measured by sieving method using the standard sieve prescribed in No. (7) in Item of Measurements, General Notices, Vol. I, Chinese Pharmacopoeia. The value of bulk density in the present invention can be obtained according to conventional methods, for example it can be measured using BT-1000 Powder Integrative Properties Tester (developed by Dandong Bettersize Instruments Co. Ltd. & Powder Technology Development Department of Tsinghua University) according to the instructions of the instrument.

The spherical granule according to the present invention requires a small amount of carrier with low single dose (commonly about 0.1-4 g per time), regular shape (spherical or sphere-like) and a smooth, round surface. The spherical granule has excellent physical properties such as good fluidity, regular distribution of particle diameter, compactness in properties, resistance to extrusion and abrasion, high density (having a bulk density of 0.6-1.3 g/ml), low specific surface area (only 0.01-0.03 m$^2$/g) and short dissolution time. The properties can improve the compliance of the patients and make popularization of the coating technique possible, thus improves defects of TCM or herbal medicine such as moisture sensitivity and instability, etc. In addition, the spherical granule according to the present invention can not only be used as common granules but also as intermediate or formula granules to prepare such dosage forms as capsule, etc. Otherwise, it can also be prepared into all sorts of coating preparations, sustaining-release or control-release preparations or site-specific sustaining-release preparations, etc.

BEST MODES OF THE INVENTION

The present invention is further described in details in combination with specific embodiments which are only applied to illustrate the invention but not to limit the scope of the invention.

EXAMPLE 1

Yangxue Qingnao Spherical Granule
1. The Extraction of Yangxue Qingnao Extractum
2.535 kg of Radix Angelicae Sinensis, 2.535 kg of Rhizoma Chuanxiong, 2.027 kg of Radix Paeoniae alba and 2.535 kg of Rhizoma Corydalis were mixed with 70% (ml/ml) ethanol and refluxed for 2 hours by heating, the reflux solution was stored elsewhere. The obtained residues, 2.027 kg of Radix Rehmanniae Preparata, 5.068 kg of Concha Margaritifera Usta, 5.068 kg of Spica Prunellae, 5.068 kg of Semen Cassiae, and 5.068 kg of Caulis Spatholobi were decocted with water for three times in the absence of Ramulus Uncariae cum Uncis, 1 hour for each. At the third decoction, 5.068 kg of Ramulus Uncariae cum Uncis was added. The decoctions were combined, concentrated under reduced pressure till the relative density was 1.09-1.13 at 55° C. Ethanol was added to the concentrate to make the final concentration of ethanol was 65% (ml/ml), allowed to stand for 24 hours, filtered, and the filtrate and the above-obtained reflux solution were combined, distilled under reduced pressure to recover ethanol till the relative density was 1.10-1.20 at 55° C. to obtain the Yangxue Qingnao extractum for later use;

2. The Preparation of Mother Granule

A mixture of dextrin and starch (1:1) was passed through 200 mesh sieve, 60 wt % thereof was added into a side-spraying spot of a fluidized bed, and additional 10 wt % thereof together with Yangxue Qingnao extractum (accounting for 15 wt % of the weight of mother granule after the liquid extract was converted to dry weight) was prepared into slurry by adding water and sprayed into the fluidized bed. Small particle with a particle diameter of 180-250 μm was screened out as mother core. Said mother core was then added into the spot and continued to spray the slurry. Simultaneously, the residual 30 wt % of the mixture of dextrin and starch (1:1) was dusted in fine powder form using dusting gun to enable the mother cores to grow, then the mother granule with a particle diameter of 300-400 μm was selected for later use;

3. The Selection of Viscosity Adjusting Agent (a) The Yangxue Qingnao extractum was diluted with 60% (ml/ml) of ethanol solution to obtain a diluent with a viscosity of 6.0-9.8 MPa·S;

(b) One drop of the diluent was dropped on a slide glass and aired. After evaporation of liquid, an intact film appeared on the surface of solid scar with high viscosity and it was easy to adhere with other granular material when contacted;

(c) The viscosity adjusting agent was selected based on such properties as viscosity, film forming ability and strength, etc. of the scar in step (b), and the experiments indicated that MCC, talc powder and micro-powder silica gel, alone or in combination, can be used as viscosity adjusting agent;

(d) A mixture of MCC and micro-powder silica gel (MCC: micro-powder silica gel=10:1), which accounted for 10 wt % of Yangxue Qingnao extractum was selected as viscosity adjusting agent, and the viscosity of the material was decreased from 9.0 MPa·S to 8.0 MPa·S;

4. The Preparation of Yangxue Qingnao Spherical Granule (a) Formulation: about 813 g of the mother granule, about 400 g of MCC (passing through 200 mesh sieve), about 40 g of micro-powder silica gel and about 4400 g of Yangxue Qingnao extractum (for 2500 doses);

(b) The mixture of MCC and micro-powder silica gel was added into the Yangxue Qingnao extractum, mixed by stirring to form a suspension with a solid content of 30 wt % (but not limited to 30 wt %) as slurry for later use;

(c) The mother granule was added into a side-spraying spot of a fluidized bed, and the slurry of step (b) was sprayed slowly till all the slurry was sprayed with a bed temperature of 35-55° C.;

(d) To the transparent coating material, water was added to prepare 7.5% (g/ml) of coating solution in bottom-spraying bed. The coating solution was sprayed in an amount corresponding to a theoretical weight gain of 3 wt % after coating to form spherical granule with a bulk density of 0.825 g/ml and dissolution time of 45 seconds;

(e) The spherical granule obtained from step (d) was encapsulated into 0# capsule with 0.525 g per capsule to obtain 10000 capsules.

EXAMPLE 2

XiaoKeQing Spherical Granule

1. The Extraction of XiaoKeQing Extractum 6 kg of Atractylodisa Rhizoma was extracted by steam distillation to obtain volatile oil of Atractylodisa Rhizoma. The residue was extracted again, filtered, and the lower layer liquid was obtained for later use. The upper layer volatile oil of Atractylodisa Rhizoma was separated and included with β-CD to obtain the inclusion complex for later use. The obtained residue, 10 kg of *Anemarrhena asphodeloides* Bunge, 6 kg of Pollen Typhae and 6 kg of Herba Euphorbiae Humifusae and 1 kg of *Coptis chinensis* Franch were decocted with water for two times, 2 hours for the first time and 1 hour for the second time. The decoctions were combined and filtered. The filtrate was combined with the lower layer liquid, concentrated to the relative density of 1.02-1.05 at 80° C. Then 95% (ml/ml) ethanol was added into the concentrate till the concentration of ethanol was 50% (ml/ml), allowed to stand, filtered, and ethanol was recovered and the concentrate with a relative density of 1.15-1.20 at 60° C. was obtained for later use.

2. The Preparation of Mother Granule 50 wt % of the inclusion complex was passed through 100 mesh sieve, and then added into a side-spraying spot of a fluidized bed. Water was added into PVP K30 containing 10 wt % of the inclusion complex to obtain solution of binder (5%, g/ml) and sprayed into the fluidized bed as slurry. Small particles with a particle diameter of 120-180 μm was screened out as mother core. Said mother core was then added into the spot and continued to spray the slurry. Simultaneously, the residual inclusion complex was dusted using dusting gun to enable the mother cores to grow, then the mother granule with a particle diameter of 200-300 μm was selected for later use;

3. The Selection of Viscosity Adjusting Agent (a) The XiaoKeQing extractum was diluted with 60% (ml/ml) of ethanol solution to obtain a diluent with a viscosity of 6.0-9.8 MPa·S;

(b) One drop of the diluent was dropped on a slide glass and aired. After evaporation of liquid, an intact film appeared on the surface of solid scar with high viscosity and it was easy to adhere with other granular material when contacted;

(c) The viscosity adjusting agent was selected based on such properties as viscosity, film forming ability and strength, etc. of the scar in step (b), and the experiments indicated that micro-powder silica gel can be used as viscosity adjusting agent;

(d) Micro-powder silica gel accounting for 7 wt % of XiaoKeQing extractum was selected as viscosity adjusting agent, and the viscosity of the material was decreased from 9.0 MPa·S to 8.0 MPa·S;

4. The Preparation of XiaoKeQing Spherical Granule (a) Formulation: about 562 g of the mother granule, the XiaoKeQing extractum (for 2000 doses) and micro-powder silica gel accounting for 7 wt % of the dry weight of the XiaoKeQing extractum;

(b) The micro-powder silica gel was added to the XiaoKeQing extractum, mixed by stirring to form a uniform suspension with a solid content of 30 wt % as slurry for later use;

(c) The mother granule was added into a side-spraying spot of a fluidized bed, and the slurry of step (b) was sprayed slowly till all the slurry was sprayed with a bed temperature of 37-55° C.;

(d) To the transparent coating material, water was added to prepare 7.5% (g/ml) of coating solution. In bottom-spraying bed, the coating solution was sprayed in an amount corresponding to a theoretical weight gain of 3 wt % after coating to form spherical granule with a bulk density of 0.93 g/ml and a dissolution time of 5 minutes;

(e) The spherical granule obtained from step (d) was encapsulated into 00# capsule with 0.75 g per capsule to obtain 10000 capsules.

EXAMPLE 3

FufangDanshen (Compound Radix Salviae Miltiorrhizae) Spherical Granule

1. The Extraction of FufangDanshen Extractum 9 kg of Radix *Salvia miltiorrhiza*, 1.76 kg of Radix Notoginseng were extracted with water for three times. The decoction was filtered, and the filtrate was concentrated and precipitated with ethanol, allowed to stand for 24 hours, filtered and concentrated to a thick paste by recovering ethanol till the relative density of the concentrate was 1.33-1.35 at 50-60° C., and the extractum was obtained. Borneol was included with cyclodextrin or PVP to form inclusion solution, and the inclusion solution was mixed well with the extractum to obtain FufangDanshen extractum for later use.

2. The Preparation of Mother Granule

A mixture of dextrin and starch (1:1) was passed through 200 mesh sieve, and then 65 wt % thereof was added into a side-spraying spot of a fluidized bed. Additionally, starch and water was mixed to prepare starch slurry (15%, g/ml) and sprayed into the fluidized bed as slurry. Small particles with a particle diameter of 180-250 μm was screened out as mother core. Said mother core was then added into the spot and continued to spray the starch slurry. Simultaneously, the residual 35 wt % of the mixture of dextrin and starch (1:1) was dusted in fine powder form using dusting gun to enable the mother cores to grow, then the mother granule with a particle diameter of 450-600 μm was selected for later use;

3. The Selection of Viscosity Adjusting Agent (a) The Fufang Danshen extractum was diluted with 60% (ml/ml) of ethanol solution to obtain a diluent with a viscosity of 6.0-9.8 MPa·S;

(b) One drop of the diluent was dropped on a slide glass and aired. After evaporation of liquid, no intact film appeared on the surface of solid scar, the film had a low viscosity, and it was easy to be scraped off as powder and severe to produce powder;

(c) The viscosity adjusting agent was selected based on such properties as low viscosity, poor film forming ability, low strength and easiness of producing powder, etc. of the scar in step (b), and the experiments indicated that a mixture of HPMC and PVP-K30 (2:5) or polyethylene glycol 6000 can be used as viscosity adjusting agent;

(d) The mixture of HPMC and PVP-K30 (2:5) was selected as viscosity adjusting agent, and the weight ratio of the mixture of HPMC and PVP-K30 to the FufangDanshen extractum was 7:25; or polyethylene glycol 6000 was selected as viscosity adjusting agent, and the weight ratio of polyethylene glycol 6000 to the FufangDanshen extractum was 18:25; and the viscosity of the material was increased from 9.0 MPa·S to 16 MPa·S;

4. The Preparation of FufangDanshen Spherical Granule (a) Formulation: about 450 g of the mother granule, polyethylene glycol 6000 (the weight ratio of polyethylene glycol 6000 to the FufangDanshen extractum was 18:25), or the mixture of HPMC and PVP-K30 (2:5) (the weight ratio of the mixture of HPMC and PVP-K30 to the FufangDanshen extractum was 7:25), 10000 doses of the FufangDanshen extractum and borneol;

(b) A solution (15 wt %) was prepared by adding anhydrous ethanol to either of the viscosity adjusting agent, said solution was added into Fufang Danshen extractum and mixed.

Then, 60% (ml/ml) of ethanol was added till a solid content was 19 wt % to obtain slurry;

(c) The mother granule was added into a side-spraying spot of a fluidized bed, and the slurry was sprayed slowly under simultaneous drying till all the slurry was sprayed to obtain spherical granule while keeping the material temperature at 37-45° C. To the transparent coating material, water was added to prepare 7.5% (g/ml) of coating solution. The coating solution was sprayed in an amount corresponding to a theoretical weight gain of 3 wt % after coating to form spherical granule with a bulk density of 0.76 g/ml and a dissolution time of 25 seconds;

(d) The spherical granule obtained from step (c) was encapsulated into 2# capsule with 250 mg per capsule to obtain 10000 capsules.

EXAMPLE 4

*Coptis chinensis* Franch Extractum Spherical Granule

1. The Extraction of *Coptis chinensis* Franch Extractum 50 kg of *Coptis chinensis* Franch was refluxed and extracted for 2 times with 75% (ml/ml) ethanol, 2 hours for each time. The extracted solutions were combined, filtered and concentrated by recovering ethanol till the relative density was 1.15-1.20 at 60° C. to obtain *Coptis chinensis* Franch extractum for later use;

2. The Preparation of Mother Granule

A mixture of dextrin and microcrystalline cellulose (1:1) was passed through 200 mesh sieve, and then 65 wt % thereof was added into a side-spraying spot of a fluidized bed. Additionally, PVP K30 and water was mixed to prepare the solution of binder (5%, g/ml) and sprayed into the fluidized bed as slurry. Small particles with a particle diameter of 180-250 μm was screened out as mother core. Said mother core was then added into the spot and continued to spray the aqueous solution of PVP K30 (5%, g/ml).

Simultaneously, the residual 35 wt % of the mixture of dextrin and microcrystalline cellulose (1:1) was dusted in fine powder form using dusting gun to enable the mother cores to grow, then the mother granule with a particle diameter of 300-400 μm was selected for later use;

3. The Selection of Viscosity Adjusting Agent (a) The *Coptis chinensis* Franch extractum was diluted with 60% (ml/ml) of ethanol solution to obtain a diluent with a viscosity of 6.0-9.8 MPa·S;

(b) One drop of the diluent was dropped on a slide glass and aired. After evaporation of liquid, no intact film appeared on the surface of solid scar, the film had a low viscosity, and it was easy to be scraped off as powder and severe to produce powder;

(c) The viscosity adjusting agent was selected based on such properties as low viscosity, poor film forming ability, low strength and easiness of producing powder, etc. of the scar in step (b), and the experiments indicated that PVP-K30 or polyethylene glycol 6000 can be used as viscosity adjusting agent;

(d) Polyethylene glycol 6000 in an amount corresponding to 28 wt % of the *Coptis chinensis* Franch extractum or PVP-K30 in an amount corresponding to 5 wt % of the *Coptis chinensis* Franch extractum was selected as viscosity adjusting agent, and the viscosity of the material was increased from 9.0 MPa·S to 16 MPa·S;

4. The Preparation of *Coptis chinensis* Franch Extractum Spherical Granule (a) Formulation: about 1000 g of the mother granule; an aqueous solution of the viscosity adjusting agent (5%, g/ml) was prepared with water;

(b) A proper amount of the *Coptis chinensis* Franch extractum (equivalent to 50 kg of crude drug) was added into the solution of the viscosity adjusting agent, water was added into the mixture and mixed by stirring to form a suspension with a solid content of 30 wt % as slurry for later use;

(c) The mother granule was added into a side-spraying spot of a fluidized bed, and the slurry was sprayed slowly under simultaneous drying till all the slurry was sprayed to obtain spherical granule. To the transparent coating material, water was added to prepare 7.5% (g/ml) of coating solution. The coating solution was sprayed in an amount corresponding to a theoretical weight gain of 3 wt % after coating to form spherical granule with a bulk density of 0.80 g/ml;

(d) 0.6 g of the spherical granule obtained from step (c) equivalents to 5 g of crude drug of *Coptis chinensis* Franch.

EXAMPLE 5

Radix Bupleuri Chinensis Extractum Spherical Granule

1. The Extraction of Radix Bupleuri Chinensis Extractum 6.25 kg of Radix Bupleuri Chinensis was refluxed and extracted for 2 times with water, 1 hour for each time. Then the extracted solution was concentrated under reduced pressure till the relative density was 1.15-1.20 at 60° C. to obtain Radix Bupleuri Chinensis extractum for later use;

2. The Preparation of Mother Granule

A mixture of dextrin and microcrystalline cellulose (1:1) was passed through 200 mesh sieve, and then 65 wt % thereof was added into a side-spraying spot of a fluidized bed. Additionally, PVP K30 and water was mixed to prepare the solution of binder (5%, g/ml) and sprayed into the fluidized bed as slurry. Small particles with a particle diameter of 180-250 μm was screened out as mother core. Said mother core was then added into the spot and continued to spray the aqueous solution of PVP K30 (5%, g/ml). Simultaneously, the residual 35 wt % of the mixture of dextrin and microcrystalline cellulose (1:1) was dusted in fine powder form using dusting gun to enable the mother cores to grow, then the mother granule with a particle diameter of 300-400 μm was selected for later use;

3. The Selection of Viscosity Adjusting Agent (a) The Radix Bupleuri Chinensis extractum was diluted with water to obtain a diluent with a viscosity of 6.0-9.8 MPa·S;

(b) One drop of the diluent was dropped on a slide glass and aired. After evaporation of liquid, an intact film appeared on the surface of solid scar, and the film had a high viscosity and a feeling of dampness;

(c) The viscosity adjusting agent was selected based on such properties as high viscosity and excellent film forming ability of the scar of the Radix Bupleuri Chinensis extractum in step (b), and the experiments indicated that polyethylene glycol 6000 can be used as viscosity adjusting agent;

(d) Polyethylene glycol 6000 in an amount corresponding to 50 wt % of the Radix Bupleuri Chinensis extractum was selected as viscosity adjusting agent and the viscosity of the material was increased from 6.0 MPa·S to 10 MPa·S;

4. The Preparation of Radix Bupleuri Chinensis Extractum Spherical Granule (a) Formulation: about 200 g of mother granule, a proper amount of the extractum (equivalent to 6.25 kg of crude drug of Radix Bupleuri Chinensis), polyethylene glycol 6000 (equivalent to the weight of Radix Bupleuri Chinensis extractum);

(b) The Radix Bupleuri Chinensis extractum and polyethylene glycol 6000 was mixed with water by stirring to form a suspension with a solid content of 20 wt % as slurry for later use;

(c) The mother granule was added into a side-spraying spot of a fluidized bed, and the slurry was sprayed slowly under simultaneous drying till all the slurry was sprayed to obtain spherical granule. To the transparent coating material, water was added to prepare 7.5% (g/ml) of coating solution. The coating solution was sprayed in an amount corresponding to a theoretical weight gain of 3 wt % after coating to form spherical granule with a bulk density of 0.60 g/ml and a dissolution time of 45 seconds;

(d) 1.0 g of the spherical granule obtained from step (c) equivalents to 6.25 g of crude drug of Radix Bupleuri Chinensis.

What is claimed is:

1. A method for preparing a pharmaceutical granule comprising a mother granule and shell layer, the preparation method comprising:

(1) producing mother granules having a diameter of from 200 μm to 750 μm, wherein the mother granules comprise a pharmaceutically acceptable carrier and/or an active pharmaceutical ingredient, selected from the group consisting of Yangxue Qingnao extractum, XiaoKeQing extractum, FufangDanshen extractum, *Coptis chinesis* Franch extractum and Radix Bupleuri Chinesis extractum, and are prepared by a process comprising:

(i) grinding and sieving a dry powder comprising a pharmaceutically acceptable carrier and/or an active pharmaceutical ingredient to obtain a particulate material with particle diameters small enough to pass through a 200 mesh sieve;

(ii) filling a first portion of the particulate material into a side-spraying or bottom-spraying spot of a fluidized bed, and spraying said first portion of the particulate material into the fluidized bed, wherein the temperature in the fluidized bed is from 40-75° C.;

(iii) mixing a second portion of the particulate material with water to form a slurry, and spraying the slurry into the fluidized bed;

(iv) screening the contents of the fluidized bed to obtain particles with a diameter of from 180 μm to 250 μm for use as mother cores;

(iv) putting the mother cores into a side-spraying or bottom-spraying spot of a fluidized bed;

(v) dusting the mother cores with a third portion of the particulate material, while simultaneously spraying the mother cores with the slurry of step (iii); and (vi) screening the contents of the fluidized bed to obtain mother granules having a particle diameter of from 200 μm to 750 μm;

(2) filling the mother granules into a fluidized bed;

(3) insufflating a gas flow into the fluidized bed;

(4) preparing a viscous suspension comprising a pharmaceutically active ingredient selected from the group consisting of Yangxue Qingnao extractum, XiaoKeQing extractum, FufangDanshen extractum, *Coptis chinensis* Franch extractum and Radix Bupleuri Chinensis extractum, wherein the suspension has a viscosity of from 6.0 to 9.8 Mpa·s and is prepared by a process comprising:

(i) diluting the active pharmaceutical ingredient with water or a pharmaceutically acceptable organic solvent, thereby producing a diluted pharmaceutical mixture in the form of a suspension having a solid content of from 15-40 wt. %; and (ii) adjusting the viscosity of the diluted pharmaceutical mixture with a viscosity adjusting agent selected from the group consisting of microcrystalline cellulose, micro-powder silica gel, polyethylene glycol, talc powder, chitosan, polyvidon, hydroxypropyl methylcellulose, and combinations thereof;

(5) spraying the mother granules with the viscous suspension of step (4) to create a shell layer, thereby producing the pharmaceutical granule; wherein the resulting pharmaceutical granule is spherical or sphere-like in shape, and has a bulk density of from 0.6 to 1.3 g/mL and a dissolution time of 0.5-5 minutes, and wherein the pharmaceutically acceptable carrier comprises from 10-60 wt. % relative to the total weight of the granule.

2. The method for preparing a pharmaceutical granule according to claim 1, wherein the temperature of the fluidized bed is 40-55° C.

3. The method for preparing a pharmaceutical granule according to claim 1, wherein the temperature of the fluidized bed is 45° C.

* * * * *